(12) United States Patent
Arnold

(10) Patent No.: US 6,673,225 B1
(45) Date of Patent: Jan. 6, 2004

(54) METHOD AND APPARATUS FOR CONCENTRATING AND/OR POSITIONING PARTICLES OR CELLS

(75) Inventor: William Michael Arnold, Wellington (NZ)

(73) Assignee: Industrial Research Limited (NZ)

( * ) Notice: Subject to any disclaimer, the term of this patent is extended or adjusted under 35 U.S.C. 154(b) by 0 days.

(21) Appl. No.: 09/701,216

(22) PCT Filed: May 29, 1999

(86) PCT No.: PCT/NZ99/00067

§ 371 (c)(1),
(2), (4) Date: Jan. 12, 2001

(87) PCT Pub. No.: WO99/62622

PCT Pub. Date: Dec. 9, 1999

(30) Foreign Application Priority Data

May 29, 1998 (NZ) ................................................ 330550

(51) Int. Cl.[7] ...................... G01N 27/447; G01N 27/453
(52) U.S. Cl. ........................................ 204/547; 204/643
(58) Field of Search ................................. 204/450, 547, 204/600, 643, 648, 553

(56) References Cited

U.S. PATENT DOCUMENTS

| 4,698,142 A | * 10/1987 | Muroi et al. | 204/544 |
| 4,956,065 A | * 9/1990 | Kaler et al. | 204/547 |
| 5,888,370 A | 3/1999 | Becker et al. | |
| 5,993,630 A | * 11/1999 | Becker et al. | 204/547 |

FOREIGN PATENT DOCUMENTS

| AU | 2756577 | 10/1981 |
| WO | WO 9411728 | 5/1994 |

OTHER PUBLICATIONS

W.M. Arnold, "Positioning, Levitation and Separation of Biological Cells," Institute of Physics Conference Series No. 163, pp 63–68 and p 93 (1999).

G. H. Markx, "Dielectrophoretic Separation of Cells: Continuous Separation," Biotechnolgy and Bioengineering, vol. 45, pp 337–343 (1995).

* cited by examiner

Primary Examiner—T. Tung
Assistant Examiner—Alex Noguerola
(74) Attorney, Agent, or Firm—Dann, Dorfman, Herrell and Skillman, P.C.

(57) ABSTRACT

A method for concentrating and/or positioning and/or separating particles or cells comprises placing a liquid medium containing the particles and/or cells over a surface having an electrode array associated with the surface, applying an alternating voltage to the electrode array to create an electric field above the surface within the medium to repel the particles or cells from the electrode array and thereby levitate the particles or cells above the surface, within the medium, by negative dielectrophoresis, and heating the liquid medium so as to cause convection currents to circulate within the medium which concentrate or relocate the levitated cells within the medium. Apparatus for concentrating and/or positioning and/or separating particles or cells are also disclosed.

39 Claims, 5 Drawing Sheets

METHOD AND APPARATUS FOR CONCENTRATING AND/OR POSITIONING PARTICLES OR CELLS

FIELD OF INVENTION

The invention comprises a method and apparatus for concentrating and/or positioning particles or cells or similar.

BACKGROUND TO INVENTION

A number of methods for concentrating particles or cells are very well known. Many frequently used methods involve centrifugation usually resulting in packing of the concentrated particles or cells at the bottom of a centrifuge tube when the medium is less dense than the particles or cells. In some circumstances this has disadvantages as it may be necessary to resuspend the particles or cells so that they may be further used. Furthermore closely packed particles or cells often adhere to one another or to the surface. One approach to overcoming these problems is to centrifuge using a concentration gradient or to centrifuge on to a small cushion of more dense medium. That approach has the disadvantage that the particles or cells then become mixed with a dense medium.

Other methods involve filtration which can also cause problems with dense packing of the particles or cells and/or drying out.

SUMMARY OF INVENTION

It is an object of the invention to provide a method for concentrating particles or cells and/or positioning these in a medium having a lower density than the density of the particles or cells, which does not involve packing of the particles or cells against a surface.

In broad terms in one aspect the invention comprises a method for concentrating and/or positioning particles or cells in a liquid medium comprising:
    subjecting the particles or cells to an electric field to levitate the particles or cells within the medium by negative dielectrophoresis, and
    heating the medium to cause convection currents within the liquid medium which concentrate or relocate the levitated cells within the medium.

More particularly the invention comprises a method for concentrating and/or positioning particles or cells comprising:
    placing a liquid medium containing the particles and/or cells over a surface having an electrode array associated with the surface,
    applying an alternating voltage to the electrode array to create an electric field above the surface within the medium to repel the particles or cells from the electrode array and thereby levitate the particles or cells above the surface, within the medium, by negative dielectrophoresis, and
    heating the liquid medium so as to cause convection currents to circulate within the medium which concentrate or relocate the levitated cells within the medium.

In broad terms in another aspect the invention comprises a method for separating particles or cells in a liquid medium comprising:
    subjecting the particles or cells to an electric field to levitate two or more different types of particles or cells within the medium to two or more different heights within the medium, and
    heating the medium to cause convection currents within the liquid medium which concentrate or relocate the levitated cells within the medium.

More particularly the invention comprises a method for separating particles or cells comprising:
    placing a liquid medium containing the particles and/or cells over a surface having an electrode array associated with the surface,
    applying an alternating voltage to the electrode array to create an electric field above the surface within the medium to repel the particles or cells from the electrode array and which thereby levitates at least two different types of particles or cells to two or more different heights above the surface, within the medium, by negative dielectrophoresis, and
    heating the liquid medium so as to cause convection currents to circulate within the medium which concentrate or relocate the levitated cells within the medium.

In broad terms in a further aspect the invention comprises apparatus for concentrating and/or positioning particles or cells in a liquid medium comprising:
    means to subject the particles or cells to an electric field to levitate the particles or cells within the medium by negative dielectrophoresis, and
    means to heat the medium to cause convection currents within the liquid medium which concentrate or relocate the levitated cells within the medium.

More particularly the invention comprises apparatus for concentrating and/or positioning particles or cells comprising:
    a surface having an electrode array associated with the surface,
    and means for containing a liquid medium containing the particles and/or cells over the surface,
    means for applying an alternating voltage to the electrode array to create an electric field above the surface within the medium to repel the particles or cells from the electrode array and thereby levitate the particles or cells above the surface, within the medium, by negative dielectrophoresis, and
    means for heating the liquid medium so as to cause convection currents to circulate within the medium which concentrate or relocate the levitated cells within the medium.

The method and apparatus of the invention may be used to concentrate and or position or reposition bacteria, fungi, protozoans or mammalian circulatory cells (e.g. from blood or lymph), viruses, inert particles such as polystyrene micro particles, which are often used as carriers for antibodies or other biologicals, nanoparticles, and similar, in immunology, diagnostics, or any other related or unrelated laboratory or industrial application. In this specification all of the above are for convenience intended to be encompassed herein by the expression "particles and cells".

The concentration is due to two sorts of localisation of the particles: above the electrode plane and also within that horizontal plane. Vertical localisation arises because the particles are denser than the medium but are repelled from close approach to the electrodes by the electric field within the medium just above the electrode array. They are levitated by a force known as negative dielectrophoresis—see Pohl, HA (1978) Dielectrophoresis, Cambridge University Press.

BRIEF DESCRIPTION OF THE FIGURES

The invention is further described with reference to the accompanying figures, by way of example and without intending to be limiting, in which.

DETAILED DESCRIPTION OF PREFERRED FORMS

Figure 1:
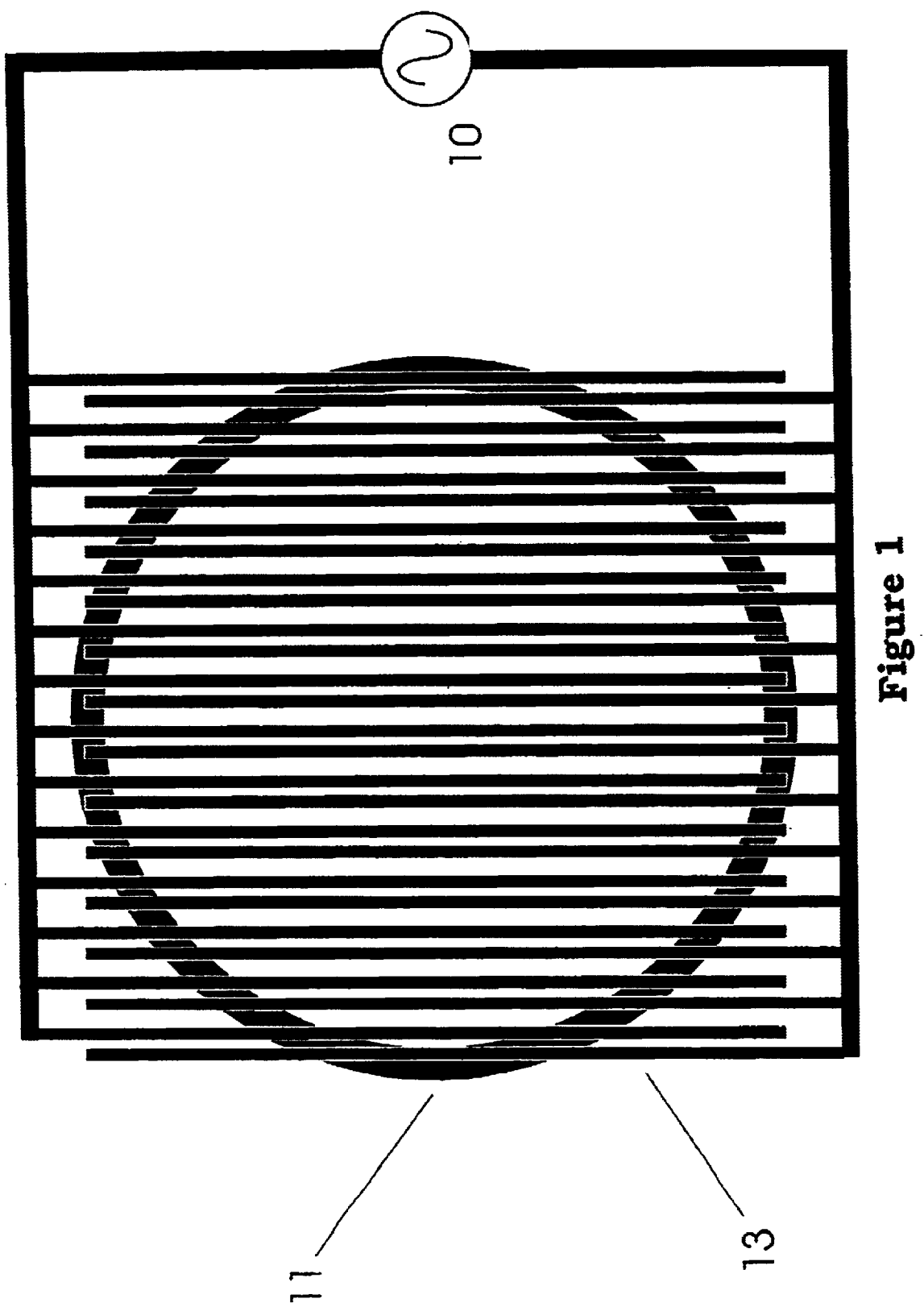
FIG. 1 is a view of an array of interdigitated electrodes on the bottom surface of a vessel or zone in which particle or cell concentration or repositioning is carried out in accordance with the invention, by which a radio frequency field is created by application of a radio frequency voltage to the electrodes to repel and levitate the particles or cells within the liquid medium by dielectrophoresis.
Figure 2:
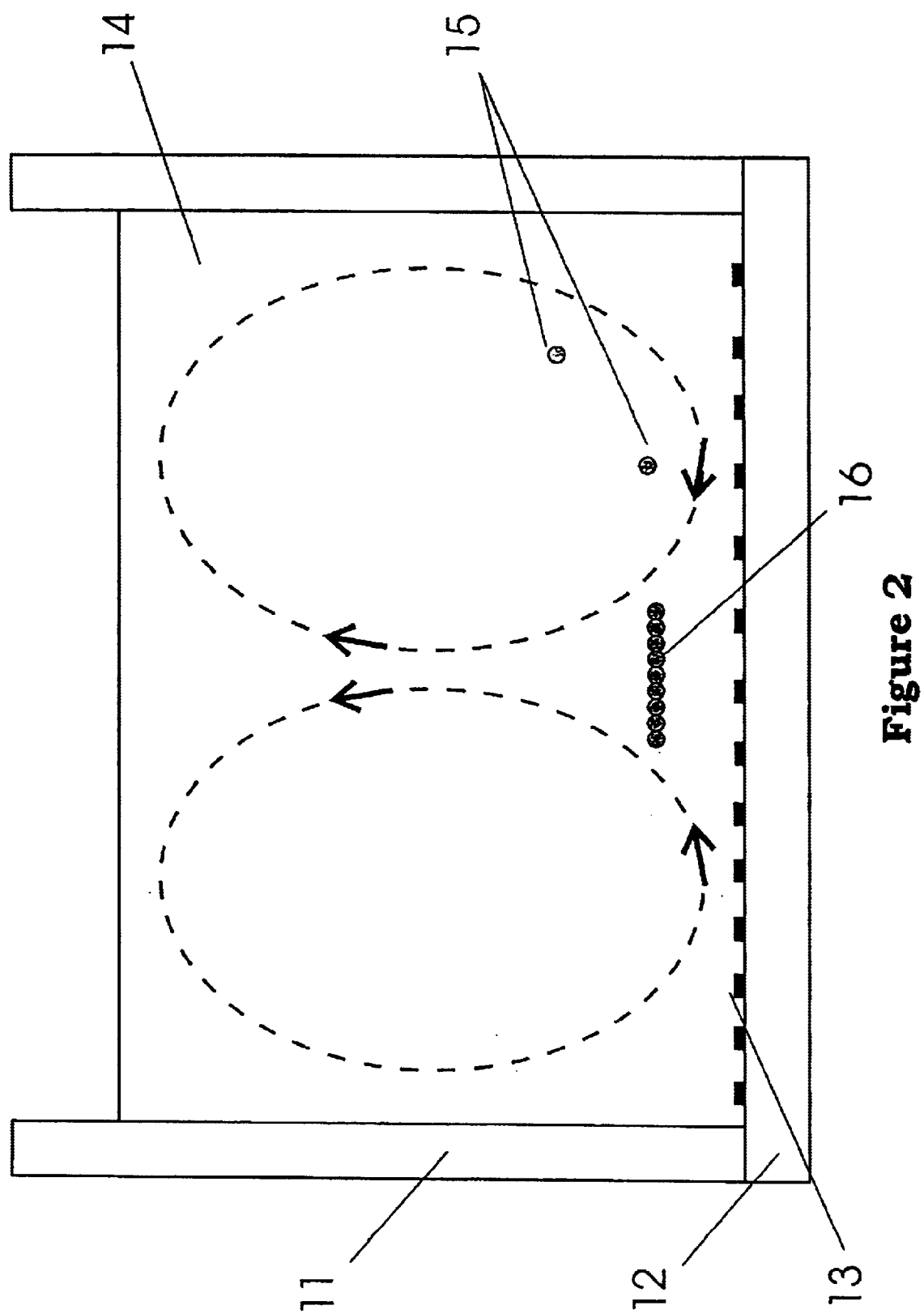
FIG. 2 is a schematic vertical cross-section view through a medium showing particle or cell concentration by the use of the invention.

The principle of the invention is further described with reference to FIGS. 1 and 2 in relation to the concentration of particles or cells within a liquid medium in a vessel, the bottom surface of which is formed of an insulator material such as glass and which carries a planar interdigitated electrode array. The vessel is shown in schematic cross-section in FIG. 2 and FIG. 1 shows in particular the electrode array. Reference numeral 11 indicates the side walls of the vessel, 12 a base of the vessel, 13 the electrode array on the base surface of the vessel, and 14 the liquid medium within the vessel. In carrying out the method of the invention a voltage is applied across the interdigitated electrodes to create an electric field above the electrodes within the medium 14. The particles or cells are repelled from the electrodes by negative dielectrophoresis, and are thereby caused to be levitated within the medium. The medium is simultaneously heated to cause convection currents indicated by dotted lines and arrows in FIG. 2 to circulate within the medium. The convection currents cause liquid at the centre of the vessel to rise, so that particles or cells 15 within the vessel are moved in a centripetal manner to concentrate at a central position above the electrode as indicated at 16, without being in physical contact with the base surface of the vessel.

Any arrangement of electrodes associated with the bottom surface of the vessel or lower part of the medium may be used to apply the electric field to the medium but in a preferred form the electrode array comprises two comb-like rows of spaced interdigitated finger-like electrode elements as particularly shown in FIG. 1. Preferably the width of each finger-like electrode element is between about 2.5 and about 50 times the average diameter of the particles or cells for any particular application, and the spacing between adjacent electrode elements is between about 5 and 100 times the particle or cell diameter. Preferably the electrode elements have a width in the range of about 4 $\mu$m to about 1000 $\mu$m and a spacing between adjacent electrode elements of between about 2 $\mu$m and about 500 $\mu$m. The voltage applied to the electrodes to create the electric field within the medium is preferably an alternating voltage of a frequency in the range 100 Hz to 1000 MHz and more preferably in the range 10 kHz to 300 MHz, and may generate a field strength within the medium in the range 10 V/mm to 100 V/mm. The field strengths required depend however on the electrode geometry, because the electrode geometry and field strength determine the field divergence. The optimum frequency, for any given particle and medium, will be determined by the frequency-dependence of the relative polarisabilities of the particle and medium. For cells, considerations of toxic effects of certain field frequencies may be necessary. Depending on the current density through the electrodes frequencies lower than 1 kHz or even 10 kHz may be disadvantageous because of electrolytic decomposition of the liquid. The levitation height will increase with the applied voltage but decrease with increasing density of the particles.

The electrode arrangement is preferably fabricated by lithography as a substantially planar structure on the surface of the bottom of the vessel in which the concentration is carried out, but alternatively may be produced by scribing or spark erosion in a metallic layer for example. The electrode geometry may be other than an array of interdigitated fingers, such as a pair of planar electrodes separated from each other by a small gap over a large area, or a twin (bifilar spiral arrangement). Electrodes of greater than 100 $\mu$m width may be made of wire also.

In the preferred form the medium is heated to create the convection currents by the same voltage applied to the electrode array 13. Alternatively however the medium may be heated by for example a separate resistance heating element provided at or near the base of the vessel for example. It may be desirable to ensure that the medium has a minimum ionic concentration to ensure heating of the medium sufficient to create the required convection currents. The medium can be water optionally containing sufficient ions and other materials to enable the survival and growth (if required) of cells. For some applications it may be useful to further increase the conductivity of the medium (say by the addition of salt) in order to elicit or increase the repulsive (levitation) force. High-dielectric substances (eg zwitterions such as amino acids, peptides, proteins and HEPES) may be added to the medium to increase its permittivity and thereby to elicit or increase the repulsive (levitation) force.

In the case of a droplet, the cooling of the sides and top of the droplet causes the convection to take the form of a circulation in which fluid at the centre rises. Observed in the horizontal plane just above the electrodes, all particles are seen to travel in a centripetal manner to a position beneath the uppermost point of the droplet. This motion follows the base of the thermal convection cell within the droplet, but the excess density of the particles prevents them rising above the levitation layer. The convection cell in the droplet sweeps out the entire column and leaves all the particles at one location. This allows concentration of particles or cells of interest, particularly bacteria, fungi, protozoans or mammalian circulatory cells.

The method of the invention may also be used to concentrate cells or particles, initially dispersed throughout a liquid medium (droplet or column) supported on a horizontal array of electrodes, in a given predeterminable position near the base of the medium. The destination is at the levitation height and at the point at which liquid (but not particles) circulates upwards. The concentrated cells or particles may be drawn off as further described. This point may be predeterminable so as to allow direct observation under a microscope without searching or refocusing. This allows considerable savings of time in the microscopic examination of fluids for low concentrations of particular cells such as pathogens. As a consequence of the known location of the destination, this facilitates the search for (and identification of) particles or cells of interest, particularly pathogenic bacteria, fungi or protozoans. The directed motion to a unique destination, causes a large concentration of the particles. Despite continuous circulation of the liquid, particles or cells may be held at the given position for hours or days and so permit analysis of development or growth in the absence of contact with a surface.

Figure 3A:
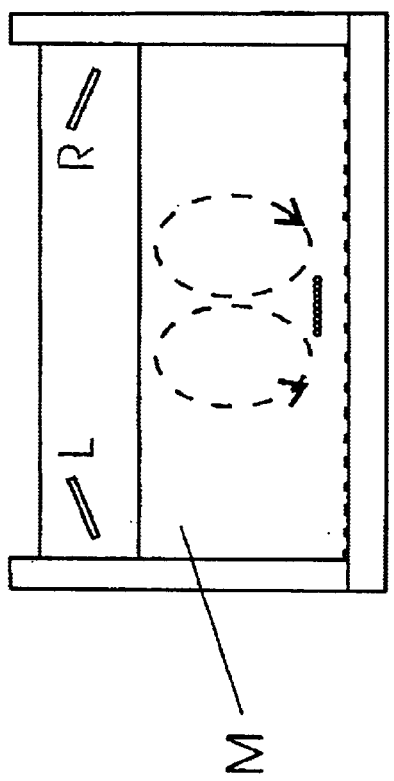
FIG. 3a is a schematic diagram similar to FIG. 2 but also showing the use of an additional electrode or electrodes above the medium to apply a further field to reshape the top surface of the medium to cause relocation of the concentrated particles or cells, in one direction as shown in FIG. 3b or another direction as shown in FIG. 3c, FIGS. 4a, 4b and 4c show the use of multiple electrodes positioned above the medium and illustrate energisation of selected electrodes to cause movement of concentrated particles or cells within the medium.
Figure 3C:
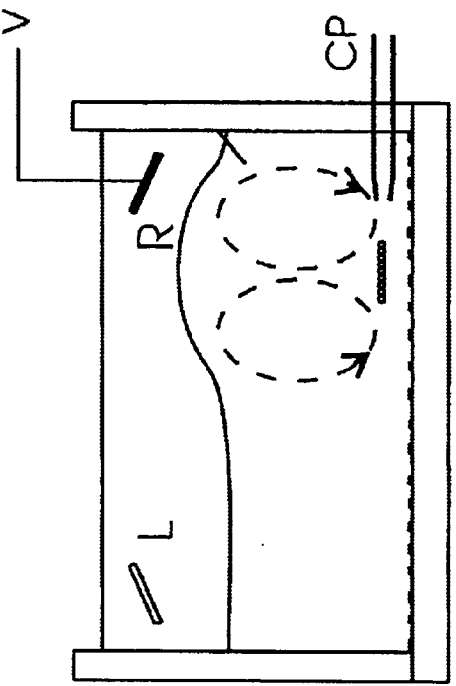
Figure 3B:
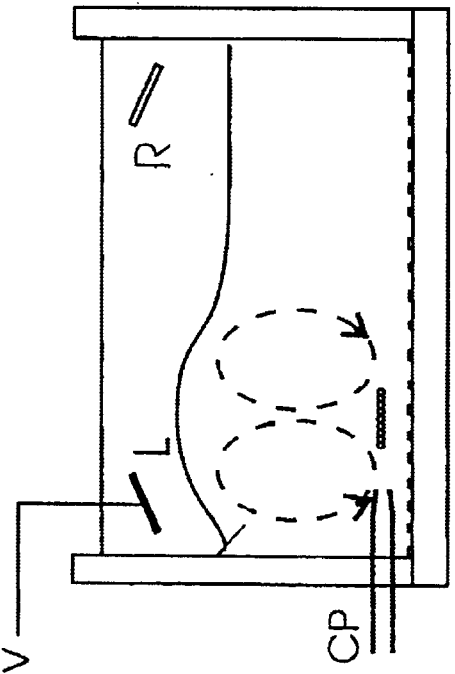

Referring to FIG. 3, one or more electrodes may be positioned adjacent the upper part of the medium to apply a voltage which electrostatically attracts the medium which reshapes a part or parts of the upper surface of the medium to cause the position at which the convection currents within the medium concentrate the particles or cells to move within the medium. In FIG. 3 either of electrodes L or R positioned adjacent the upper part of the medium may have selectively applied thereto a voltage which reshapes the upper surface of the medium and moves the position at which the convection currents occur towards one or other side of the vessel to also move the concentrated particles or cells to one or other side of the vessel. In FIG. 3b application of a voltage to electrode L causes the medium to be attracted to that electrode thereby causing the concentrated particles or cells to shift to that side of the vessel. If the other electrode R has a voltage applied thereto, as shown in FIG. 3c the medium will be attracted to that electrode and the raft of concentrated particles or cells will be caused to move to the other side of the vessel. These electrodes are preferably positioned within a layer of low conductivity above the liquid medium containing the particles or cells, such as a fluid layer of low conductivity which is immiscible with the medium. Hydrocarbons or silicone oil for example may be used for this purpose. Alternatively the electrodes above the medium may simply be separated from the top surface of the medium by an air gap. Collection capillaries CP as shown in each of FIGS. 3b and 3c may be used to draw off the concentrated particle cells, and thus the electrodes L and R may be used to shift the cells after concentration in the centre of the vessel towards the collection outlet. The position of the convection currents within the medium may also be caused to move, to move or reposition the concentrated particles or cells within the medium, by other means such as a fluid jet impinging on the opposite side of the surface of the medium to that at which the cell collection is to be directed, or a vertical strip of metallisation could be applied to the wall of the vessel where the medium is relatively non-conductive, to which a voltage is then applied to cause the liquid to ascend by electro-capillary force, for example.

Figure 4:
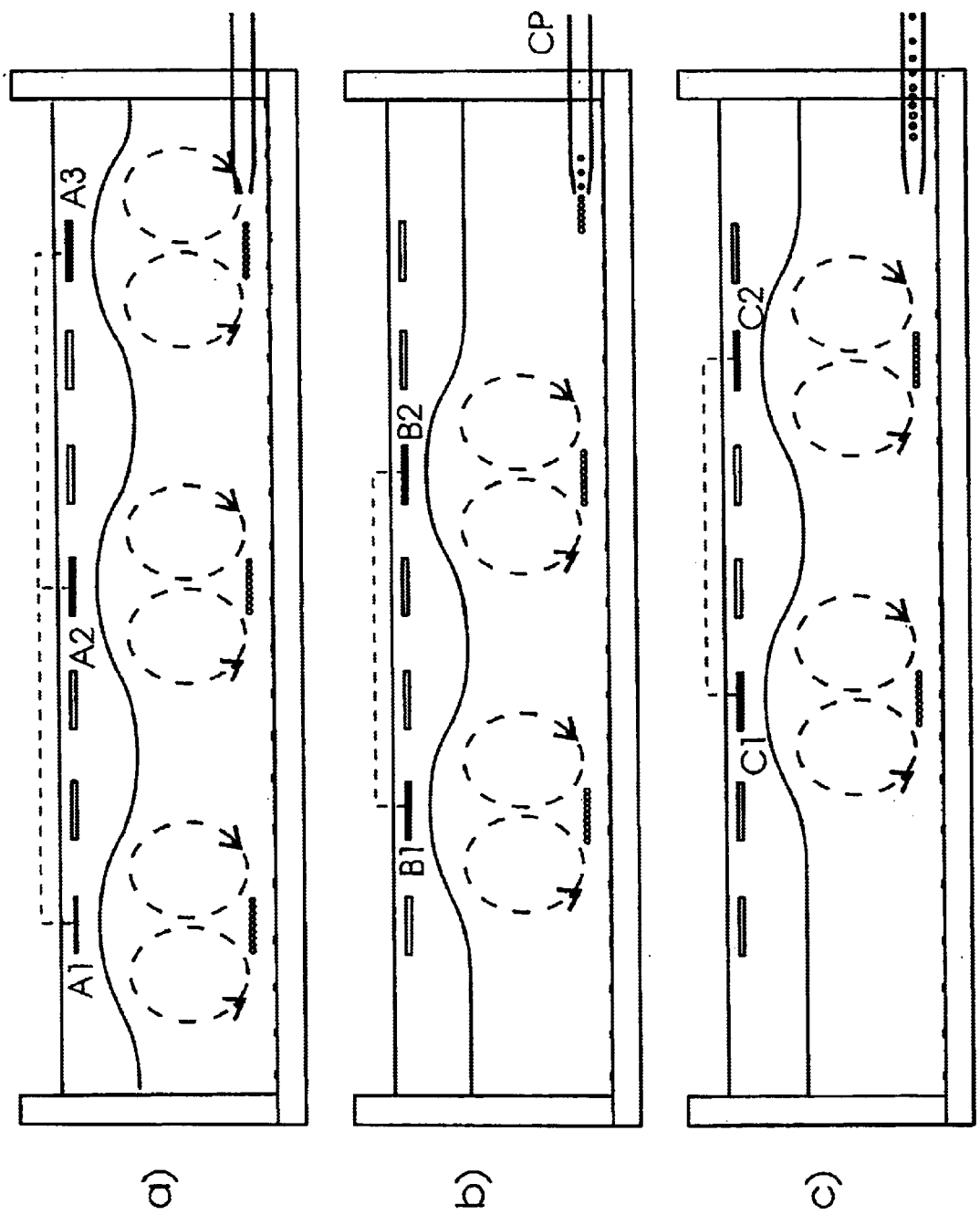

FIGS. 4a to 4c show a further arrangement in which a series of electrodes is positioned adjacent the upper part of the medium, which may be selectively energised to cause movement of the particles or cells through the medium. By selective application of a voltage to any of the electrodes positioned over the surface of the medium the fluid meniscus can be raised locally beneath that electrode, and so determine that convection circulation takes place in that region. When electrodes A1, A2 and A3 are energised as shown in FIG. 4a, convection currents occur beneath those three electrodes to concentrate the particles or cells. When next electrodes B1 and B2 are energised as shown in FIG. 4a, whilst maintaining the levitation voltage applied to the microelectrode array on the bottom surface, the convection currents and the particle or cells are caused to move, to the right in the diagram page, while when electrodes C1 and C2 are subsequently energised there is a second step to the right.

Repetition of this sequence enables sequential movement of the rafts of particles or cells to the outlet capillary CP, so that the particles or cells may be withdrawn batch wise.

Figure 5:
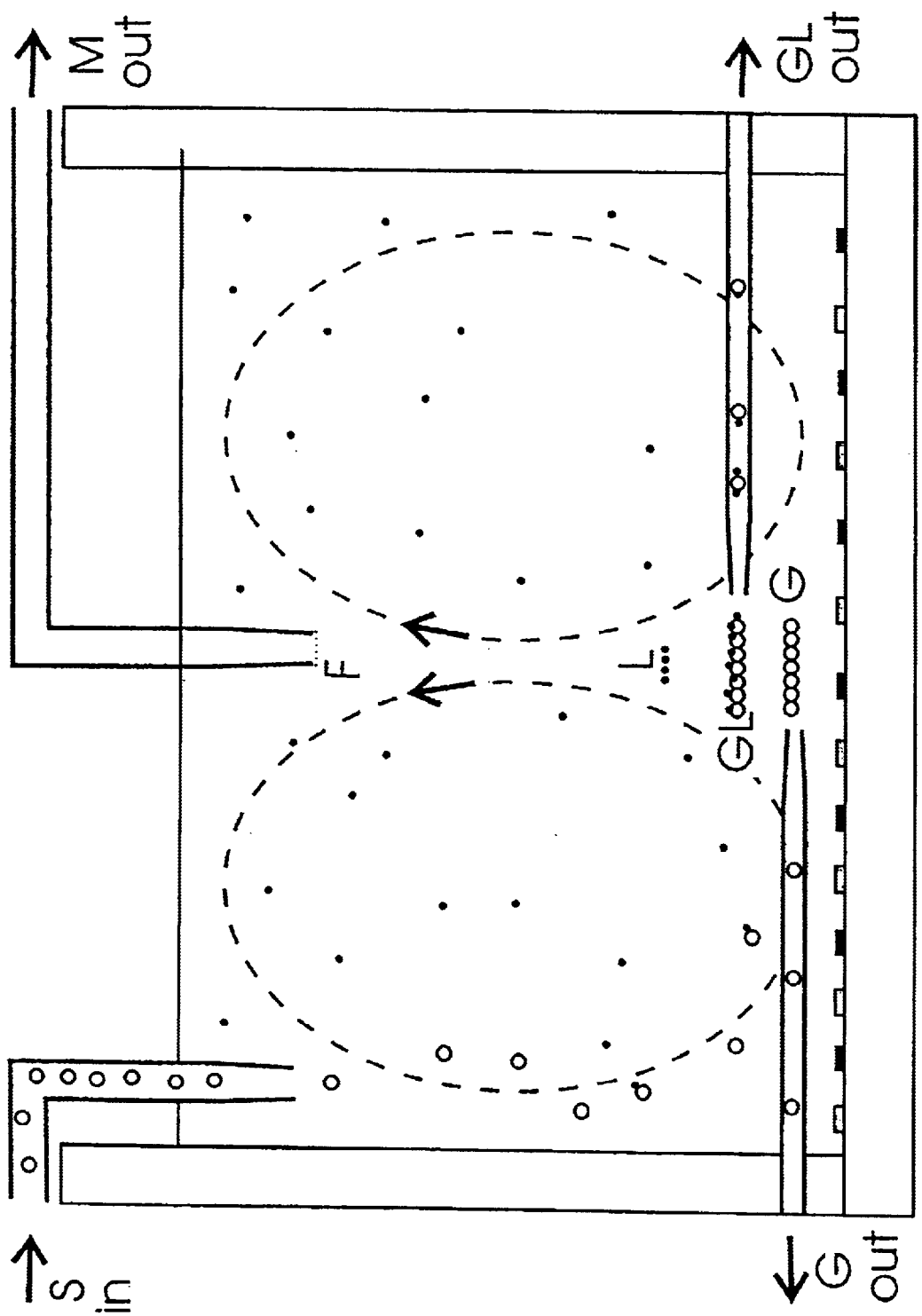
FIG. 5 shows the use of the method of the invention to separate particles or cells having different levitation properties.

FIG. 5 shows use of the method and apparatus of the invention in another way to separate cells or particles having distinct levitation properties from each other. There are some populations of cells (which are of interest to immunologists or pathologists) that appear identical and have no known dielectric or density differences, but often differ in surface markers, which may be revealed by antibodies selective for them. Normally, separation based on these antibodies requires them to have a fluorescent or magnetic label, so that the antibody-labelled cells may be separate in a FACS (fluorescence activated cell-sorter) or by their response to a magnetic field gradient. Such sub-populations of cells differing only in surface antigens may be separated using the method of the invention. Referring to FIG. 5 the mixed population of cells S are fed in to a circulation that already contains a large number of antibody-coated particles L. Such particles may be surface-modified polystyrene microparticles (polystyrene latex), which are known to possess low values of electrical permitivity and conductivity compared to the solutions used for cell cultivation, and therefore have limit negative values of polarisability factor U' over a wide range of frequencies. The force producing levitation is proportional to the divergence of the electric field and to the negative polarizability of the cell or particle relative to the medium in which it is suspended. This relative polarizability is quantitatively described by the read part (U') of the Clausius-Mossotti factor, often represented by U (see Foster K R, Sauer F A and Schwan H P, 1992 Biophys. J. 63 180–190). Levitation of the particle only occurs if this force overcomes the effective gravitational downforce on the particle in the liquid (the negative buoyancy). Due to the fact that the field divergence decreases as the distance from the electrode array increases, heavy particles or those will only slightly negative values of U' will be levitated only slightly above the array, whereas particles with density only slightly more than that of the liquid, and those with the most negative values of U', will be levitated to the greatest heights above the array. In addition, they have a density only slightly greater than that of water. Accordingly, the particles levitate very easily in an electric field, and most are set into circulation rather than forming a levitated raft, however a few may form a concentrated raft shown as L. The antibodies on the particles are selective for the desired sub-population of cells, to which they bind irreversibly. Mixing of cells and particles is assured due to the number of particles in the circulation.

Cells which have none of the desired surface marker form a raft at G, whilst cells which have the desired surface marker form a raft at a greater height, due to the more powerful levitation force exerted upon the bound microparticles. It is possible that several rafts GL will be formed due to the possibility that just one or else multiple microparticles bind to a given cell. It may be useful to set the frequency applied to the levitation electrode array at the bottom of the vessel away from optimum for cells G so as to give a decreased levitation height for G, but an increased separation between G and GL.

It may be helpful to prevent non-specific binding between antibody-coated-microparticles and cells by including 1–100 mg/ml of serum albumen, non-specific immunoglobulins or other macromolucules in the circulation, or by other methods known to those skilled in the art of immunology.

The separated populations of cells are withdrawn through capillary tubes as indicated at G out and GL out. If the volume of S added is considerable, it may be necessary to remove excess medium through a tube M out and this should be covered with a filter F to prevent loss of microparticles.

The following examples further illustrate the invention.

EXAMPLE I

A droplet of 30 μl (microlitres) volume is pipetted onto a planar interdigitated electrode array consisting of gold strips deposited lithographically on glass. The electrodes are 5 mm long and of 40 μm width and 40 μm separation. A radio-frequency voltage (1 volt peak at 5 MHz) is applied between adjacent electrode strips. The droplet contains 50 mmole/l KCl and also yeast cells (about $10^6$/ml) derived from a stationary culture grown in yeast extract (1%) and glucose (1%). Over the course of 15 minutes, the cells are observed to move towards a collection point at the centre of the droplet and form a close-packed mass there. The cells are observed to be levitated by about 15 μm above the plane of the electrodes.

EXAMPLE II

In order to prevent evaporation, a similar arrangement to the above was covered by a layer of liquid paraffin. The apparatus was sterilised with ethanol, and the droplet contained sterile growth medium (1% yeast extract, 2% glucose) to which some yeast cells (about 200) were added. The cells were observed to collect above the centre of the base of the droplet. Over a period of 5 hours, the cells grew and divided with a mean generation time of 2 h 15 minutes.

The above examples are intended to illustrate the invention. The invention may be practised with numerous modifications and variations as will be apparent to those skilled in the art. For example numerous different types of particles, cells, media, treatment times volumes and electrode arrangements may be used.

What is claimed is:

1. A method for concentrating and positioning particles or cells in a liquid medium comprising:
    subjecting the particles or cells to an electric field to levitate the particles or cells within the medium by negative dielectrophoresis, and
    heating the medium to cause convection currents within the liquid medium which relocate the particles or cells substantially in a horizontal direction and thereby concentrate and position the levitated particles or cells within the medium.

2. A method for concentrating and positioning particles or cells comprising:
    placing a liquid medium containing particles and/or cells over a surface having an electrode array associated with the surface,
    applying an alternating voltage to the electrode array to create an electric field above the surface within the medium to repel the particles or cells from the electrode array and thereby levitate the particles or cells above the surface, within the medium, by negative dielectrophoresis, and
    heating the liquid medium so as to cause convection currents to circulate within the medium which relocate the particles or cells substantially in a horizontal direction and thereby concentrate and position the levitated particles or cells within the medium.

3. A method according to either of claims 1 and 2 including subjecting the particles or cells to an electric field created by an alternating voltage of a frequency in the range of 10 kHz to 300 kHz.

4. A method according to either of claims 1 or 2 wherein the strength of the electric field generated with the medium is in the range 10 V/mm–100 V/mm.

5. A method according to either of claims 1 or 2 wherein the medium is also heated to cause said convection currents by a radio frequency electric field.

6. A method according to claim 2 wherein the electrode array comprises at least two comb-like rows of spaced interdigitated finger-like electrode elements.

7. A method according to claim 6 wherein the width of each finger-like electrode element is between about 2.5 and 50 times the average diameter of the particles or cells, and the spacing between adjacent electrode elements is between about 5 and 100 times the particle or cell diameter.

8. A method according to either of claims 6 or 7 wherein the electrode elements have a width in the range about 4 μm to about 1000 μm and a spacing between adjacent electrode elements of between about 2 μm and about 500 μm.

9. A method for concentrating particles and/or cells comprising:
    placing a liquid medium containing the particles and/or cells over a surface having an electrode array associated with the surface,
    applying an alternating voltage to the electrode array to repel the particles or cells from the electrode array and thereby levitate the particles or cells above the surface, within the medium, by negative dielectrophoresis, and
    heating the liquid medium so as to cause convection currents to circulate within the medium including rising currents centrally within the medium over the electrode array which relocate the particles or cells in a horizontal direction and thereby concentrate and position the levitated particles or cells within the medium.

10. A method according to claim 9 wherein the medium is also heated to cause said convection currents by the voltage applied to the electrode array.

11. A method for repositioning particles and/or cells within a liquid medium comprising:
    subjecting the particles and/or cells to an electric field within the medium which repels the particles or cells to thereby levitate the particles or cells within the medium,
    heating the liquid medium to cause convection currents within the medium which relocate the particles or cells in a horizontal direction and thereby concentrate and position the levitated particles or cells within the medium, and
    applying a force to cause the concentrated particles or cells to move across the medium.

12. A method for repositioning particles and/or cells within a liquid medium comprising:
    subjecting the particles and/or cells to an alternating voltage to create an electric field within the medium which repels the particles or cells to thereby levitate the particles or cells within the medium,
    heating the liquid medium to cause convection currents within the medium, and
    subjecting the upper part of the medium to a second electric field which reshapes a part or parts of the upper surface of the medium to thereby cause the position at which the convection currents within the medium concentrate the cells to move within the medium.

13. A method according to claim 12 wherein said second electric field is applied via at least one electrode positioned above the top surface of the medium.

14. A method according to claim 12 including applying a voltage selectively to one or more of a series of electrodes positioned adjacent the upper part of the medium to cause movement of the particles or cells through the medium.

15. A method according to either of claims 13 and 14 wherein said electrode or electrodes are positioned within a layer of low conductivity above the liquid medium containing the particles or cells.

16. A method according to claim 15 wherein said layer of low conductivity comprises a layer of low conductivity fluid which is immiscible with the liquid medium containing the particles or cells and which extends above the liquid medium containing the particles or cells.

17. A method according to either of claims 11 or 12 including drawing off the particles or cells from the medium after relocation of the particles or cells within the medium.

18. A method for separating particles or cells in a liquid medium comprising:
   subjecting the particles or cells to an electric field to levitate two or more different types of particles or cells within the medium to two or more different heights within the medium, and
   heating the medium to cause convection currents within the liquid medium which relocate the particles or cells substantially in a horizontal direction and thereby concentrate and position the levitated particles or cells within the medium.

19. A method according to claim 18 wherein the electrode array comprises at least two comb-like rows of spaced interdigitated finger-like electrode elements.

20. A method for separating particles or cells comprising:
   placing a liquid medium containing the particles and/or cells over a surface having an electrode array associated with the surface,
   applying an alternating voltage to the electrode array to create an electric field above the surface within the medium to repel the particles or cells from the electrode array and which thereby levitates at least two different types of particles or cells to two or more different heights above the surface, within the medium, by negative dielectrophoresis, and
   heating the liquid medium so as to cause convection currents to circulate within the medium which relocate the particles or cells substantially in a horizontal direction and thereby concentrate and position the levitated particles or cells within the medium.

21. A method according to either one of claims 18 and 20 including selectively drawing off at least one of the concentrated types of particles or cells.

22. A method according to either of claims 18 or 20 wherein the alternating voltage is of a frequency in the range 10 kHz to 30 MHz.

23. A method according to either of claims 18 or 20 wherein the field strength generated within the medium is in the range 10 V/mm–100 V/mm.

24. A method according to either of claims 18 ro 20 wherein the medium is also heated to cause said convection currents by a radio frequency electric field.

25. Apparatus for concentrating and positioning particles or cells in a liquid medium comprising:
   means to subject particles or cells to an electric field to levitate the particles or cells within the medium by negative dielectrophoresis, and
   means to heat the medium to cause convection currents within the liquid medium which relocate the particles or cells substantially in a horizontal direction and thereby concentrate and position the levitated particles or cells within the medium.

26. Apparatus for concentrating and positioning particles or cells comprising:
   a surface having an electrode array associated with the surface,
   means for containing a liquid medium containing particles and/or cells over the surface,
   means for applying an alternating voltage to the electrode array to create an electric field above the surface within the medium to repel the particles or cells from the electrode array and thereby levitate the particles or cells above the surface, within the medium by negative dielectrophoresis, and
   means for heating the liquid medium so as to cause convection currents to circulate within the medium which relocate the particles or cells substantially in a horizontal direction and thereby concentrate and position the levitated particles or cells within the medium.

27. Apparatus according to claim 26 wherein the electrode array comprises at least two comb-like rows of spaced interdigitated finger-like electrode elements.

28. Apparatus according to claim 27 wherein the electrode elements have a width in the range about 4 $\mu$m to about 1000 $\mu$m and a spacing between adjacent electrode elements of between about 2 $\mu$m and about 500 $\mu$m.

29. Apparatus according to either of claims 25 or 26 also comprising means for applying a force to cause the concentrated particles or cells to move across the medium.

30. Apparatus according to either of claims 25 or 26 also comprising means for subjecting the upper part of the medium to a second electric field which electrostatically attracts part or parts of the upper surface of the medium to thereby alter the position at which the convection currents within the medium concentrate the particles or cells to move the concentrated articles or cells within the medium.

31. Apparatus according to claim 30 wherein said means for applying a second electric field comprises at least one electrode positioned above the top surface of the medium.

32. Apparatus according to claim 30 wherein said means for applying a second electric field comprises a series of electrodes positioned adjacent the upper part of the medium and means to apply a voltage selectively to electrodes in the series to cause movement of the particles or cells through the medium.

33. Apparatus for separating particles or cells in a liquid medium comprising:
   means to subject the particles or cells to an electric field to levitate two or more different types of particles or cells within the medium to two or more different heights within the medium, and
   means to heat the medium to cause convection currents within the liquid medium which relocate the particles or cells substantially in a horizontal direction and thereby concentrate and position the levitated particles or cells within the medium.

34. Apparatus according to claim 33 wherein the electrode array comprises at least two comb-like rows of spaced interdigitated finger-like electrode elements.

35. Apparatus for separating particles or cells comprising:
   means to contain a liquid medium containing the particles and/or cells over a surface having an electrode array associated with the surface,
   means for applying an alternating voltage to the electrode array to create an electric field above the surface within the medium to repel the particles or cells from the electrode array and which thereby levitates at least two different types of particles or cells to two or more different heights above the surface, within the medium, by negative dielectrophoresis, and means for heating the liquid medium so as to cause convection currents to circulate within the medium which relocate the particles or cells substantially in a horizontal direction and thereby concentrate and position the levitated particles or cells within the medium.

36. Apparatus according to either one of claim 33 and 35 including means for selectively drawing off at least one of the concentrated types of particles or cells.

37. Apparatus according to either of claim 33 and 35 wherein the alternating voltage is of a frequency in the range of 10 kHz to 300 MHz.

38. Apparatus according to either of claims 33 or 35 wherein the field strength generated with the medium is in the range 10 V/mm–100 V/mm.

39. Apparatus according to either of claim 33 or 35 wherein the medium is also heated to cause said convection currents by a radio frequency electric field.

* * * * *

UNITED STATES PATENT AND TRADEMARK OFFICE
CERTIFICATE OF CORRECTION

PATENT NO. : 6,673,225 B1  Page 1 of 1
APPLICATION NO. : 09/701216
DATED : January 6, 2004
INVENTOR(S) : William Michael Arnold It is certified that error appears in the above-identified patent and that said Letters Patent is hereby corrected as shown below:

Col. 7, line 66
"300kHz" should read -- 300MHz --

Col. 9, line 50
"30MHz" should read -- 300MHz --.

Signed and Sealed this

Twenty-third Day of October, 2007

JON W. DUDAS
*Director of the United States Patent and Trademark Office*